United States Patent [19]

Wong

[11] 4,286,587
[45] Sep. 1, 1981

[54] VAGINAL DRUG DELIVERY SYSTEM MADE FROM POLYMER

[75] Inventor: Patrick S. Wong, Kowloon, Hong Kong

[73] Assignee: ALZA Corporation, Palo Alto, Calif.

[21] Appl. No.: 113,499

[22] Filed: Jan. 21, 1980

Related U.S. Application Data

[60] Continuation-in-part of Ser. No. 950,454, Oct. 11, 1978, Pat. No. 4,215,691, which is a division of Ser. No. 775,718, Mar. 9, 1977, abandoned.

[51] Int. Cl.³ .............................................. A61F 5/46
[52] U.S. Cl. ..................................... 128/127; 128/260
[58] Field of Search ................ 128/127, 130, 260, 261

[56] References Cited

U.S. PATENT DOCUMENTS

| 3,967,618 | 7/1976 | Zaffaroni | 128/260 |
|---|---|---|---|
| 3,993,073 | 11/1976 | Zaffaroni | 128/260 |
| 3,995,633 | 12/1976 | Gougeon | 128/260 |
| 4,012,496 | 3/1977 | Schöpflin et al. | 128/260 |
| 4,066,075 | 1/1978 | Hughes | 128/127 |
| 4,144,317 | 3/1979 | Higuchi et al. | 128/260 |

*Primary Examiner*—C. Fred Rosenbaum
*Attorney, Agent, or Firm*—Paul L. Sabatine; Edward L. Mandell

[57] ABSTRACT

An intravaginal therapeutic system for the pre-programmed, unattended delivery of a drug is disclosed. The system comprises (a) a drug, (b) a delivery module comprising a reservoir for storing the drug in an amount for execution of the program, a rate controller which maintains the rate of drug delivered in a therapeutically effective amount throughout the life of the system, an energy source for transferring drug from the reservoir to the vagina, and a portal for releasing the drug from the module to the vagina, (c) a platform which integrates the module into a unit sized, shaped and adapted for insertion and retention in a vagina, and (d) therapeutic program which provides for the controlled release of drug to produce a beneficial effect over a prolonged period of time.

25 Claims, 4 Drawing Figures

VAGINAL DRUG DELIVERY SYSTEM MADE FROM POLYMER

CROSS-REFERENCE TO COPENDING APPLICATION

This patent application is continuation-in-part of U.S. patent application Ser. No. 950,454 filed on Oct. 11, 1978, now U.S. Pat. No. 4,215,691 issued on Aug. 5, 1980 which application is a division of U.S. patent application Ser. No. 775,718 filed on Mar. 9, 1977, now abandoned. This application, application Ser. No. 950,454 and application Ser. No. 775,718 both are all assigned to the ALZA Corporation of Palo Alto, Calif.

FIELD OF THE INVENTION

This invention pertains to an intravaginal system. The system comprises a drug, a delivery module, a platform and a therapeutic program that operates as a unit for delivering an effective amount of drug to the vagina. More specifically, the invention relates to an intravaginal therapeutic system manufactured from a thermoplastic polymer in the form of an intravaginal device for delivering a beneficial drug to a vagina over a prolonged period of time.

BACKGROUND OF THE INVENTION

Vaginal devices for delivering a drug are known to the prior art. For example, U.S. Pat. No. 3,545,439 issued to Gordon W. Ducan discloses an intravaginal ring-shaped device that can be made of varying types of polymeric materials. The device is formed of a solid polymer containing drug that is released by diffusion to the vagina. The device optionally contains a tension spring for keeping it in the vagina. In U.S. Pat. No. 3,920,805 patentee Theodore J. Roseman discloses a solid, polymeric device that has a nonmedical central solid core and an encircling medicated coating of the polymer. The device releases drug by diffusion and in a preferred embodiment, the device is ring-shaped with a flat tensioning spring molded in the nonmedicated central core.

While, the above-described devices are useful for certain applications, serious disadvantages are frequently associated with these devices that limit their use. For example, generally the polymers used by the prior art are thermoset polymers which require molding and curing fabrication procedures to form solid devices. These fabrication procedures tend to restrict the shape of the device, and the use of said polymers limits the amount of drug that can be loaded into the polymer and leads to a more rigid device. Those versed in the art will recognize that if vaginal devices can be provided made of materials that are essentially free from the above tribulations, such devices would be a valuable advancement in the art and a useful improvement.

OBJECTS OF THE INVENTION

Accordingly, it is an immediate object of this invention to provide an improved intravaginal delivery system for the controlled and continuous delivery of a drug over a prolonged period of time.

Yet another object of the invention is to provide an intravaginal system comprising materials easy to fabricate into systems and which materials can release drugs at meaningful rates over a prolonged period of time.

Yet still another object of the invention is to provide an intravaginal delivery system that is flexible, can have high drug loading, and which system can deliver drugs at a controlled and useful rate over prolonged period of time.

Another object of the invention is to provide an intravaginal delivery system manufactured with vaginally compatible materials for releasing drugs over a prolonged period of time.

Other objects, features, aspects, and advantages of the invention will be more apparent to those versed in the art from the following detailed specification, taken in conjunction with the accompanying claims.

SUMMARY OF THE INVENTION

This invention concerns an intravaginal system useful for delivering drugs. The system comprises a wall made of a non-toxic, thermoplastic polymer surrounding a reservoir containing an inner mass transfer conductor and a drug. The wall and the carrier are permeable to the passage of drug by diffusion, but the permeability of the wall to the passage of drug is lower than through the carrier. Since the permeability through the wall is lower, passage through the wall is the rate determining step for releasing an effective amount of drug from the operable system to the vagina.

BRIEF DESCRIPTION OF THE DRAWINGS

In the drawings, which are not drawn to scale, but are set forth to illustrate various embodiments of the invention, the figures are as follows.

DETAILED DESCRIPTION OF THE DRAWINGS

Figure 1:
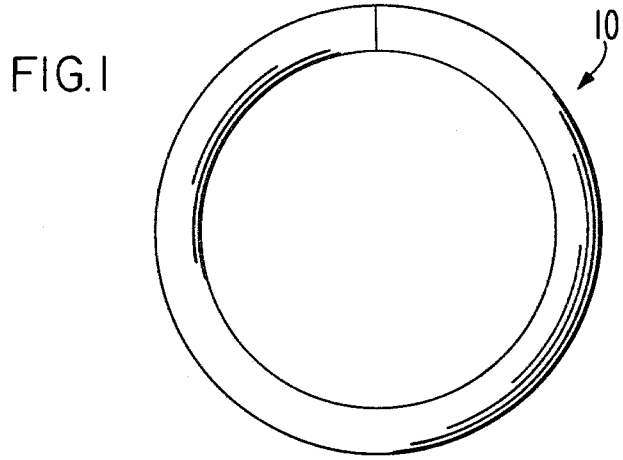
FIG. 1 illustrates an intravaginal system sized, shaped, and adapted for insertion and retention in a vagina.

Turning now to the drawings in detail, which are examples of intravaginal systems that can be used for releasing a drug to the vagina for the management of health and disease, and which examples are not to be construed as limiting the invention, one embodiment thereof is seen in FIG. 1 and identified by the numeral 10. The phrase "intravaginal delivery system" as used herein refers to a controlled dosage form which provides pre-programmed, unattended delivery of drug, and for a time period, established to meet a specific therapeutic and beneficial need.

Figure 2:
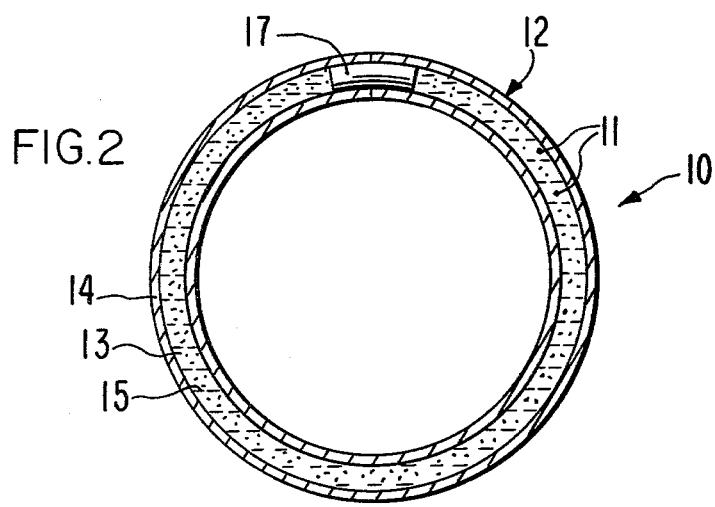
FIG. 2 illustrates the intravaginal system of FIG. 1 as seen in a cross-section, opened view and manufactured with means for forming a unit device and an internal reservoir.

System 10, as seen in FIG. 2, comprises a drug 11, selected for producing a desired physiologic or pharmacologic effect when delivered to the target receptor site, the vagina, and a delivery module 12. Delivery module 12 is essentially the body of system 10 and it comprises (a) a reservoir 13 for storing an amount of drug 11 required for execution of the prescribed therapeutic program, (b) a rate controller 14, or wall formed of a thermoplastic polymer that maintains the prescribed rate of drug administered throughout the life of system 10, (c) an energy source 11, or the concentration of drug 11 in reservoir 13 that provides the driving means for transferring drug 11 from a higher amount in reservoir 13 to rate controller 14, (d) an inner mass transfer conductor 15 for housing drug 11 in reservoir 13, (e) a portal 14, which in this invention is a rate controller 14 that provides for the exit of drug 11 from module 12 to the vagina, and (f) a coupling member 17 made for uniting the module into a single annular shaped system. In FIG. 2, coupling member 17 is a solid material placed inside the module to form an end-to-end fluid-tight connection, for successful use of system 10 during release of drug 11.

Figure 3:
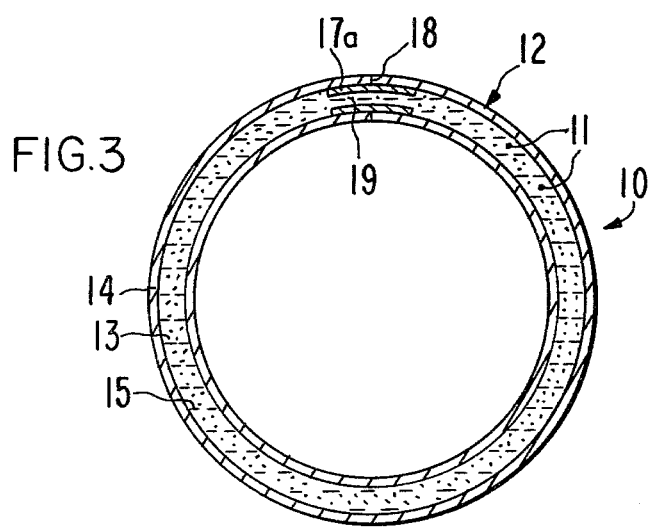
FIG. 3 depicts the vaginal system of FIG. 1 in opened view made with a means for forming an integral system which means is a different embodiment than the means illustrated in FIG. 2.

FIG. 3 illustrates a vaginal system 10 that is similar to the system illustrated in FIG. 2, with all the numbers as described in FIG. 2, except for the numbers discussed immediately below. In FIG. 3, number 17a represents a coupling member used as a joint for joining the ends, represented by a single line 18, of system 10 into an end-to-end essentially fluid impervious joint. Coupling 17a, in this embodiment, has a passageway 19 therethrough that permits the passage of a liquid mass transfer conductor 15 to flow in reservoir 13. In both embodiments, 17 and 17a, the coupling member is in mated relation with the inside of module 12 to form an essentially liquid-tight union.

System 10, in the above Figures, comprises drug 11 stored in module 12 which module 12, is integrated into a unit sized, shaped, structured and adapted as a platform for placing in the vagina, can embrace many shapes. That is, the platform can have various continuous, curved shapes. Mainly, system 10 embraces a presently preferred single annular shape, which annular shape includes ring, oval, ellipse, toroidal, and like appearing annular shapes. The novel system 10 can be used for delivering drugs 11 to animals, warm-blooded mammals including humans and primates, farm animals and laboratory animals. The dimensions of the system will vary depending on the host and the shape used for delivering the drug. For example, at its maximum dimension the device will measure from one loci on the wall to a distant loci on the wall of from 0.4 cm to 16 cm, with presently preferred devices exemplified by an annular shaped system which can have an external diameter of from 0.5 cm to 14 cm, with general dimensions for various hosts as follows: humans 6 cm to 12 cm, sheep 2 cm to 7 cm, dogs 0.5 cm to 5.0 cm, swine 2 cm to 7.5 cm, household cats 0.4 cm to 4 cm, and dairy cattle 5 cm to 12 cm.

DETAILED DESCRIPTION OF THE INVENTION

In accordance with the practice of this invention, it has now been unexpectedly found that certain vaginally acceptable thermoplastic polymeric materials can be used for forming rate controller 14 of intravaginal system 10 for the controlled release of drug 11, for example by diffusion. The use of these materials is unexpected because these materials can be successfully used substantially free of any adverse affects on the vagina. The vagina is lined with an extremely delicate tissue, and it is essential, therefore, that materials forming system 10 do not adversely effect the vagina. The thermoplastic materials used for the purpose of this invention are the vaginally compatible materials set forth below. By compatible is meant the materials are pharmaceutically acceptable within the environment of the vagina and generically to the host. That is, these materials do not break down in the vagina, there is no absorption of the materials, there is no deleterious action on the sensitive tissues in the area of placement and retention of the system over a prolonged period of time, and the materials do not harm drugs and carriers housed in system 10.

The thermoplastic polymers suitable for the purpose of this invention include polymers, copolymers and the like, that are capable of being softened by heating and hardened by cooling through a temperature range characteristic of the polymer, its crystalline melting or glass transition temperature, and in the softened state they can be shaped by flow into systems by molding or extrusion. The change for these materials upon heating is substantially physical. One preferred example of a thermoplastic polymer that can be used for the present purpose is styrene-butadiene block copolymer. The styrene-butadiene block copolymer useful for manufacturing rate controller 14 includes those generally formed by initiation at a chain end of an already formed polymeric chain. The block copolymers are thermoplastic elastomers because of their ability to become fluid and moldable at elevated temperatures. These properties lend themselves to the manufacture of system 10. The block copolymer useful for the present purpose can be represented by the following general formula:

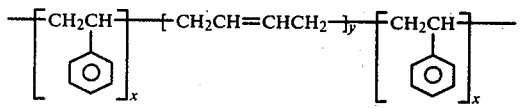

wherein x is $5 \times 10^1$ to $10 \times 10^4$ and y is $1 \times 10^3$ to $2 \times 10^4$. Generally, in a more preferred range the styrene block copolymer will have a molecular weight in the range of 10,000 to 20,000 and the butadiene will have a molecular weight in the range of 40,000 to 100,000. The styrene butadiene block copolymers suitable for the present purpose are permeable to drugs, including antifertility, effective amounts of progestational and estrogenic vaginally-administered steroids.

Additional thermoplastic polymers that can be used for manufacturing system 10 include poly(methylacrylate), poly(butylmethacrylate), plasticized poly(vinylchloride), plasticized nylon, plasticized soft nylon, plasticized poly(ethylene terephthalate), poly(ethylene), poly(acrylonitrile), poly(trifluorochloroethylene), poly(4,4'-isopropylene diphenylene carbonate), poly(ethylene-vinyl esters), poly(ethylene-vinyl acetate), poly(vinylchloride-diethyl fumarate), poly(esters of acrylic and methacrylic), partially hydrolyzed poly(vinyl acetate), poly(vinyl butyral), poly(amides), poly(vinyl carbonate), poly(urethane), poly(olefins), and the like. These polymers and their physical properties are known to the art and they can be synthesized according to the procedures disclosed in Encyclopedis of Polymer Science and Technology, Vol. 15, pages 508 to 530, 1971, published by Interscience Publishers, Inc., New York; *Polymers*, Vol. 17, 938 to 956, 1976; *Technical Bulletin* SCR-159, 1965, Shell Corp., New York; and references cited therein.

Exemplary inner mass transfer conductors 15, include carriers that are suitable of housing drug 11 in reservoir 13, including liquid, semi-liquid carriers such as emulsions, glycols, and the like. These carriers are permeable to the passage of drugs, they are capable of containing dissolved and undissolved drugs, and they are capable of forming a liquid carrier wall interface at the inner surface of wall 14. Typical carriers include a member selected from the group consisting of mineral, animal, fruit, nut, plant, sylvan, inorganic and organic oils. The liquid carriers also include a member selected from the group consisting essentially of glycols, alkylene glycols, dialkylene glycols, poly(alkylene glycols), poly(oxyalkylene)-poly(oxyalkylene)copolymer, and the like. The carriers also include aqueous carriers such as water, saline, and buffers. Representative of carriers include vegetable oil, marine oil, aqueous media such as water mixed with poly(alkylene glycols) including poly(ethylene glycols) having a molecular weight of 400 to 6000, poly(propylene glycol) having a molecular weight of 500 to 2000, glycerol polysorbate 80, and the like. Examples of carriers are known to the art in *Pharmaceutical Sciences*, by Remington, 1970, published by Mack Publishing Company, Easton, Pa.

The term drug as used herein includes any physiologically or pharmacologically active substances that produces a local or systemic effect when released in a biological environment, a vagina. The active drug can be inorganic, or organic compounds including drugs that act on the nervous system, drugs that act on tissues, muscles and organs, analgesics, anti-inflammatory, prostaglandins, anti-microbial, anti-viral, anti-fungal, hormones, and the like. The beneficial drugs and their conventional doses are known in *Remington's Pharmaceutical Sciences*, 14th Edition, 1970, published by Mack Publishing Company, Easton, Pa.; and in *The Pharmacological Basis of Therapeutics*, by Goodman and Gilman, 4th Edition, 1970, published by MacMillian Company, London.

Representative drugs, in a presently preferred embodiment include anti-fertility steroids. In the specification and the accompanying claims, the phrase anti-fertility steroid and the term steroid are used interchangeably and they broadly include progestational substances that have antifertility properties and estrogenic substances that have anti-fertility properties. These substances can be of naturally occurring or synthetic origin and they generally possess a cyclopentanophenanthrene nucleus. The term progestational substance as used herein embraces progestogen which term is used in the pharmaceutically acceptable steroid art to generically describe steroids possessing progestational activity, and the former also includes progestines, a term widely used for synthetic steroids that have progestational effects. The active anti-fertility progestational agents that can be used to produce the desired effects in mammals, including humans, and primates, include without limitations: pregn-4-ene-3,20-dione, also known as progesterone; 19-nor-pregn-4-ene-3,20-dione; 17-hydroxy-19-nor-17α-preng-5(10)-ene-20-yn-3-one; dl-11α-ethyl-17-ethynyl-17-α-hydroxygon-4-ene-3-one; 17ethynyle-17-hydroxy-5(10)-estren-3-one; 17α-ethyinyl-19-norestosterone; 6-chloro-17-hydroxypregna-4,6-diene-3,20-dione; 17α-hydroxy-6α-methyl-17(-1-propynl-)androst-4-ene-3-one; 9α, 10α-pregna-4,6-diene-3,20-dione; 17α-hydroxy-17α-pregn-4-ene-3,20-dione; 17-hydroxy-17α-pregn-4-ene-20-yne; 19-nor-17α-preg-4-ene-20yne-17-diol; 17α-hydroxyprogesterone; 17-hydroxy-6α-methylpregn-4-ene-3,20-dione; mixtures thereof and the like.

The term estrogenic and estrogenic anti-fertility agents as used herein also includes the compounds known as estrogens that possess anti-fertility properties including α-estradiol, α-estradiol 3-benzoate, 17-α-cyclopentane propionate estradiol, 1,3,5(10)-estratriene-3,17α-diol dipropionate, estra-1,3,5(10)-triene 3,17α-diol valerate, estrone, ethynyl estradiol, 17-αethynyl estradiol-3-methyl ether, 17-ethinyl estradiol-3-cyclopentoether, estriol, mixtures thereof, and the like. Generally, reservoir 13 will contain from 100 nanograms to 5 grams of progestational or estrogenic steroid for release at the rate of 0.05 micrograms to 50 milligrams per day, and in a presently preferred range of 0.5 milligrams to 6.0 milligrams per day to the vagina of adult child bearing woman. Generally, the system can be used from a period of 1 day to 1 year, or longer.

Additionally, the above progestational and estrogenic agents can be in the form of their pharmacologically accepted derivatives, such as their hydroxy or keto groups can be in a derivative form for the present purpose. The progestational or estrogenic derviative used should easily convert to the parent agent upon its release from the device by biological activities such as enzymatic transformation, pH assisted hydrolysis in the vagina, tissue and metabolism and the like. The derivative can also be used to control the solubility of the agent in the liquid core and to assist in metering the agent from the device. Suitable derivatives include without limitation, esters with pharmaceutically acceptable acids such as acetate, glucuronate, benzoate, propionate, butyrate, valeroate, hexanoate, heptanoate, maleate, citrate, succinate, tartrate, fumarate, malate, ascorbate, sulphate, phosphate and the like; ethers such as lower alkoxy-tetrahydropyran-yl, unsubstituted tetrahydropyran-yl, silyl moieties, trifluoromethyloxy, cyclopentylenol ethers and other functional groups such as ureido, and the like.

The materials used for manufacturing the coupling member are generally physiologically inert materials. The coupling member can be made from the same material as the vaginal system, or the coupling member can be made from a different material than the materials used to make the vaginal device. The coupling member, when placed inside a tubular wall forming the system has the same shape as the system and it cooperates with the tube to form a single, annular device. The coupling generally has a diameter measured across its cross-section equivalent to the inside diameter of the tubular member forming the system. Typical materials for forming the coupling are those listed above. Also, the coupling can be made from a hydrophilic polymer, such as a sparingly to moderately cross-linked hydrogel that swells 5 to 20% when in place in the presence of a fluid carrier in the system. Representative hydrophilic polymers include polyglycolmethacrylate, copolymeric diethylene glycolmethacrylate and methylmethacrylate, polyacrylonitrile, polymethacrylamide, polyhydroxylathyl methacrylate, and the like.

The coupling used for joining the two end can be held in firm, fluidtight relation by solvent bonding, or by adhesive attachment. When a solvent is used, the surfaces of the coupling, and the inside of the tube are moistened with an organic solvent that causes the surfaces to feel tacky, and when placed in contact the surfaces then bond and adhere in a fluidtight union. The ends of the member can be adhesively united to form a closed system by applying an adhesive substance to the surfaces that hold the ends together by surface attachment. For the above procedures, the solvent include organic solvents such as methylene chloride, ethylene dichloride, trichlorobenzene, dioxan, isophorone, tetrahydrofuran, aromatic and chlorinated hydrocarbons, mixed solvents, such as 50/50 ethylene dichloride/diacetone alcohol; 40/60 alcohol/toluene; 30/70 alcohol/carbon tetrachloride, and the like. Suitable adhesive include natural adhesives and synthetic adhesives, such as, animal, nitrocellulosic, polyamide, phenolic, amino, epoxy, isocyanate, acrylic, silicate, organic adhesives of polymers, and the like. The adhesives are known to the art in *The Encyclopedia of Chemistry*, Second Edition, edited by George L. Clark and Gessner G. Hawley, 1966, published by VanNostrand Reinhold Co., Cincinnati, Ohio; and the solvents are known in *Encylopedia of Chemical Technology*, Kirk-Othmer, Sec. Ed., Vol. 16, 1969, published by Interscience, Publishers Inc., New York.

The following examples are merely illustrative of the present invention and they should not be considered as limiting the scope of the invention in any way, as these examples and equivalents thereof will become apparent to those versed in the art in the light of the present disclosure, the drawings and the accompanying claims.

EXAMPLE 1

Figure 4:
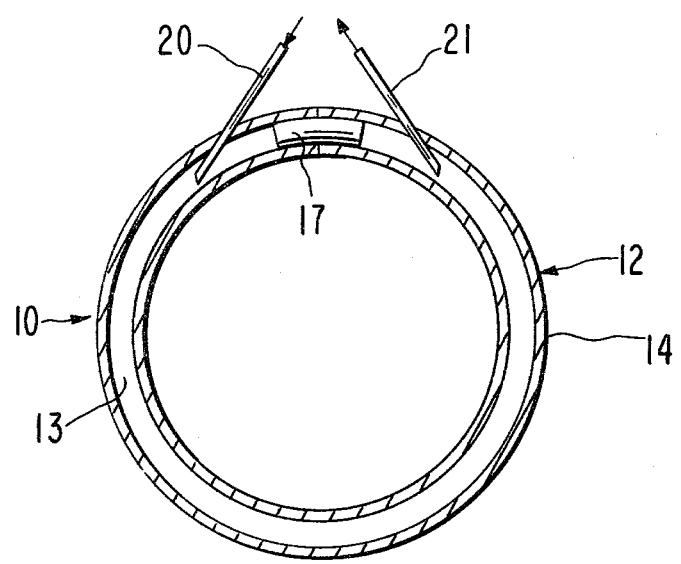
FIG. 4 illustrates the vaginal system of FIGS. 1 to 3 in opened section showing means for filling the system.

Intravaginal systems used for the purpose of this invention were manufactured as follows: First, a section of the styrene butadiene block copolymer vaginal acceptable tubing was washed with water for 48 to 56 hours, and then dried in air at room temperature. Then, the tubing was cut into appropriate lengths and shaped like a ring, as seen in FIG. 4, and molded into a torus at 165° C. Next, a solid polymeric plug 17, made of the copolymer, and having an outside diameter equivalent to the inside diameter of the tube was very lightly dampened with methylene chloride and inserted into the tube for joining the opened tube at its two ends, thereby forming a closed system. Then the hollow ring was filled by injecting a steroid carrier mixuture into reservoir 13 through inlet port or needle 20 with continuous filling of reservoir 13 until all the air is displaced through outlet port or needle 21. This procedure completely fills reservoir 13. Finally, the needle punctures were sealed with a little methylene chloride. Reservoir 13 was filled with progesterone in polyethylene glycol having a molecular weight of 400, 5% wt/wt.

EXAMPLE 2

Following the general procedure of Example 1, additional systems 10 were prepared having a toroidal shape and made with the same copolymer. The systems were manufactured with an internal placed coupling in mated relation with the inside of the tube to form a single toroidal system. The systems were made with a wall 14 having a thickness of $1.78 \pm 0.08$ mm, an internal diameter of 6 mm, an outside diameter of 4.4 cms, and a reservoir containing 35% progesterone and 65% polyethylene glycol having a molecular weight of 600.

EXAMPLE 3

The procedure of Example 2 was repeated with conditions as described except the systems of this example had a toroidal shape with a wall thickness of $2.79 \pm 0.08$ and the reservoir housed 50% progesterone and 50% polyethylene glycol having a molecular weight of 600. The other dimensions were as described previously.

EXAMPLES 4-5

The procedures of Examples 1 to 3 are repeated with the couplings or inserts made of poly(vinylchloride) with a passage therethrough, or of cross-linked poly(glycolmethacrylate). The couplings 17 are positioned inside the tubular member and they extends from the ends of the member a distance therein that imparts both structural support and continuity to the manufactured closed, annular ring. The cooperation of the couplings with the member acting as a unit provides a system suitable for intimate anatomical contact and for beneficial drug release within a vagina.

APPLICATION OF THE INVENTION

The delivery of steroids at meaningful rates from three systems made according to the mode of the invention was measured from three toroidal shaped systems. The results were as follows: (1) a system having a wall thickness of $2.79 \pm 0.08$ mm and a progesterone loading of 0.7 gr had a steady state of release rate of $5.63 \pm 0.24$ mg per day; (2) a system having a wall thickness of $1.78 \pm 0.08$ mm and a progesterone loading of 1.3 gr had a steady state release rate of $9.49 \pm 0.25$ mg per day; and (3) a system having a wall thickness of $0.75 \pm 0.08$ mm and a norethindrone loading of 0.4 gr had a steady state release rate of $0.56 \pm 0.07$ mg per day as measured over a prolonged period of 120 days.

Also, systems containing norethisterone were placed in the vagina of fertile women. The systems were comfortable and well-received by the vagina and the host. The systems are preferably placed between the rear endometrial wall of the vagina and the upper edge of the pubic bone. In this place, the medicating system releases a contraceptively effective amount of steroid over a prolonged period of 75 days to yield the intended effect.

It will be understood to those versed in the art in the light of the present specification, drawings and the accompanying claims that the invention makes available to the art both a novel and useful vaginal system for delivering progestational and estrogenic steroids to produce a desired antifertility effect; and, the rate of release from these systems can be controlled to product this effect, while simultaneously overcoming the problems associated with the prior art. It will be further understood to those versed in the art that different embodiments of this invention can be made without departing from the spirit and the scope of the invention. Accordingly, it is to be understood the invention is not to be construed as limited, but it embraces all equivalents inherent herein.

I claim:

1. A method for delivering a drug to a vagina, said method comprising the steps of:
   a. positioning in a vagina a device for delivering a drug, said device consisting essentially of:
      1. a continuous curved shaped body sized and adapted for easy positioning and comfortable retention in a vagina, said body consisting of;
      2. a wall formed of a non-toxic tubular shaped, thermoplastic moldable polymeric material, united at its ends by a coupling placed in the tubular wall in mated relation with the inside of the wall to form as essentially liquidtight union, which wall surrounds and defines;
      3. an internal reservoir;
      4. a drug housed in the reservoir in an amount for performing a therapeutic program;
      5. a carrier for the drug in the reservoir; and
   b. delivering the drug at a preprogrammed, unattended continuous and controlled rate through the wall in a therapeutically effective amount to a vagina over a prolonged period of time for performing the therapeutic program.

2. A method for delivering a drug to a vagina according to claim 1 wherein the coupling is made of the same polymeric material forming the device.

3. A method for delivering a drug to a vagina according to claim 1 wherein the coupling is made of a different polymeric material than the material that forms the device.

4. A method for delivering a drug to a vagina according to claim 1 wherein the coupling is a solid insert.

5. A method for delivering a drug to a vagina according to claim 1 wherein the coupling has passageway therethrough for the carrier to flow in the reservoir.

6. A method for delivering a drug to a vagina according to claim 1 wherein the device at its maximum dimensions measures from a loci on its curved body to a loci on its distant curved body of from 0.4 cm to 16 cm.

7. A method for delivering a drug to a vagina according to claim 1 wherein the device annular shaped for easy positioning and comfortable retention in the vagina.

8. A method for delivering a drug to a vagina according to claim 1 wherein the device is a single annular shaped body adapted for easy positioning and comfortable retention in the vagina.

9. A method for delivering a drug to a vagina according to claim 1 wherein the carrier is a liquid carrier for the drug.

10. A vaginal device for delivering drugs, said device consisting essentially of:
   a. a closed, curved body sized and shaped as a platform adapted for easy insertion and comfortable retention in a vagina, said body consisting essentially of:
   b. a wall formed of a tubular shaped, non-toxic, thermoplastic, moldable polymeric material united at its ends by a coupling inserted in the tubular wall and having a diameter approximately equivalent to the inside diameter of the tubular wall, to form an essentially liquid impervious union, with the wall surrounding and forming;
   c. an internal reservoir;
   d. a drug housed in the reservoir;
   e. a carrier for the drug in the reservoir; and,
   f. wherein, said platform at its maximum dimensions measures from a loci on its curved wall to a loci on its distant curved wall of from 0.4 cm to 16 cm, and when placed in a vagina will provide a preprogrammed, unattended continuous delivery of drug at a controlled rate and in a therapeutically effective amount to a vagina over a prolonged period of time.

11. The vaginal device for delivering drug according to claim 10 wherein the coupling inserted in the tubular wall is made of the same polymeric material forming the wall.

12. The vaginal device for delivering drug according to claim 10 wherein the coupling inserted in the tubular wall is made of a different polymeric material than the polymeric material forming the wall.

13. The vaginal device for delivering drug according to claim 10 wherein the coupling inserted in the tubular wall is made as a solid, polymer insert.

14. The vaginal device for delivering drug according to claim 10 wherein the coupling has a passageway therethrough for the carrier to flow in the reservoir.

15. The vaginal device for delivering drug according to claim 10 wherein the coupling is solvent bonded to the inside of the tubular wall.

16. The vaginal device for delivering drug according to claim 10 wherein the coupling is adhesively joined to the tubular wall.

17. The vaginal device for delivering drug according to claim 7 wherein the device is a single annular platform.

18. The vaginal device for delivering drug according to claim 7 wherein the carrier is a liquid carrier for the drug in the reservoir.

19. A device for delivering a drug to a vagina, said device consisting essentially of:
   a. an annular ring sized and adapted for easy insertion and comfortable retention in a vagina, said ring consisting of:
   b. a tubular shaped wall having a pair of ends and made of a vaginally acceptable thermoplastic, moldable polymer;
   c. a coupling within the tubular wall at its ends and in mated relation therewith to form an end-to-end liquidtight connection;
   d. an internal reservoir within the tubular wall;
   e. a drug housed in the reservoir;
   f. a carrier for the drug in the reservoir; and,
   g. wherein, said device when in operation in a vagina will deliver drug at a preselected, unattended, continuous and controlled rate, and in a vaginally acceptable amount to the vagina over a prolonged period of time.

20. The device for delivering drug to a vagina according to claim 19 wherein the coupling is made from a hydrophilic polymer that swell is the presence of fluid in the reservoir.

21. The device for delivering drug to a vagina according to claim 14 wherein the carrier is a member selected from the group consisting essentially of a liquid, emulsions and glycols.

22. The device for delivering drug to a vagina according to claim 19 wherein the carrier is an oil selected from the group consisting of mineral, animal, fruit, nut, plant, sylvan, organic and inorganic oils.

23. The device for delivering drug to a vagina according to claim 19 wherein the carrier is a member selected from the group consisting of a glycol, alkylene glycol, dialkylene glycols, poly(oxyalkylene)-copolymer, and mixtures thereof.

24. The device for delivering drug to a vagina according to claim 19 wherein the carrier is a member selected from the group consisting of water, saline and buffers.

25. The vaginal device for delivering drug according to claim 19 wherein the carrier is a fluid carrier for the drug in the reservoir.

* * * * *